United States Patent [19]

Teramoto et al.

[11] Patent Number: 5,119,823
[45] Date of Patent: Jun. 9, 1992

[54] CUFF WRAPPING APPARATUS FOR BLOOD PRESSURE METER

[75] Inventors: Tsutom Teramoto, Nagaoka Kyo; Masamichi Okada; Mikio Takada, both of Kyoto, all of Japan

[73] Assignee: Omron Corporation, Kyoto, Japan

[21] Appl. No.: 564,460

[22] Filed: Aug. 8, 1990

[30] Foreign Application Priority Data

Aug. 8, 1989 [JP] Japan ................... 1-205261

[51] Int. Cl.⁵ .............................. A61B 5/02
[52] U.S. Cl. ........................... 128/686; 606/202
[58] Field of Search ............ 128/686, 677, 678, 672, 128/674, 679, 684, 687, 690, 668; 606/201, 202, 203; 24/273, 274 R, 274 WB, 30.5 L, 30.5 R; 30/162

[56] References Cited

U.S. PATENT DOCUMENTS

| | | | |
|---|---|---|---|
| 2,020,469 | 10/1934 | Laufman et al. | 128/686 |
| 3,280,511 | 9/1964 | Johnson | 49/323 |
| 3,888,002 | 6/1975 | Graham | 30/162 |
| 3,935,984 | 2/1976 | Lichowsky | 128/2.05 |
| 4,206,765 | 6/1980 | Huber | 128/686 |
| 4,226,020 | 10/1980 | Quenot et al. | 30/162 |
| 4,263,697 | 4/1981 | Speedie | 24/30.5 L |
| 4,274,424 | 6/1981 | Kimura et al. | 128/686 |
| 4,761,882 | 8/1988 | Silverstein | 30/162 |
| 5,005,290 | 4/1991 | Gilbert | 30/162 |

FOREIGN PATENT DOCUMENTS 0073123  3/1983  European Pat. Off. .
2191587 12/1987 United Kingdom .

OTHER PUBLICATIONS

Proceedings of the Seventh Annual Conference of the IEEE/Engineering in Medicine and Biology Society-Americana Congress Hotel, Chicago, Ill., Sep. 27-30, 1985, J. C. Lin et al, vol. 1 of 2.

Primary Examiner—Max Hindenburg
Assistant Examiner—Guy V. Tucker
Attorney, Agent, or Firm—Foley & Lardner

[57] ABSTRACT

A cuff wrapping apparatus has a casing and a cuff. A lever base to which the leading tip of the cuff is fixed, is slidably provided with respect to the case, both in cuff winding and cuff releasing directions. Also, a movable lever is provided on the lever base. The movable lever is also movable in cuff winding and cuff releasing directions. An elastic body is placed between the lever base and the lever in order to transfer force applied to the lever. A lever base fixing mechanism fixes the lever base to the casing. A moving piece which moves with the lever enables the lever base fixing mechanism to enter either a fixing state or a releasing state, in accordance with the force applied to the lever.

18 Claims, 5 Drawing Sheets

CUFF WRAPPING APPARATUS FOR BLOOD PRESSURE METER

BACKGROUND OF THE INVENTION

1. Field of the Invention

The present invention relates generally to a cuff mechanism for blood pressure meters. More specifically, it relates to a finger cuff for an oscillometric sphygmomanometer.

The oscillometric method of determining blood pressure through detection of pulse oscillations was first reported by Roy and Adami in 1890. In the method, blood pressure is determined indirectly, as opposed to actually sticking a needle in the bloodstream, by occlusion of an artery by cuff pressurization. When cuff pressure is high enough to close an artery and thus stop the flow of blood, the pressure can be gradually released and compared to the blood flow returning to the artery. However, not until recently with the invention of computers and microprocessors has man been able to take advantage of this method.

2. Description of the Related Art

The oscillometric method of determining blood pressure has traditionally involved mainly the optical oscillation method. In the optical oscillation method, a light emitting diode (LED) inside the cuff beams infrared light into the body. Since blood inside the artery absorbs more infrared than other living tissues, the amount of infrared that is exposed to a phototransistor (PTr) is a function of the blood volume in the artery. One disadvantage with this method is its reliance on light for measurement. Measurements conducted in daylight risk inaccuracy due to sunlight interfering with the infrared light. Another disadvantage with an optical oscillometric apparatus is that cuff construction for such a device is complicated and costly due to the infrared elements. Not only are the photoelectric devices expensive in and among themselves, but also they restrict bladder construction. The bladder construction must conform to the necessity of the photoelectric devices to be properly aligned with respect to the artery. Thus, bladders in the prior art contain many ridges which expand together in order to tighten the cuff. Although this allows the LED and the PTr to maintain proper alignment, the complex construction is more expensive and less effective than the simple bladder employed in this invention. First, the ridges reduce the accuracy of the measured blood pressure because the measurement is a function of the bladder's surface area contact with the skin. Secondly, the need for fitting all sizes of fingers necessitates a large initial diameter into which voluminous air pressure must be pumped.

Reference is made to Oku U.S. application Ser. No. 533,835, filed Jun. 6, 1990 and assigned to the assignee of the instant application.

SUMMARY OF THE INVENTION

To overcome the parameters imposed on cuff construction by the optical oscillation method, it is a primary object of this invention to utilize a blood pressure measuring apparatus that employs a cuff oscillation method to determine blood pressure. The cuff oscillation method measures blood pressure through tiny fluctuations in the cuff pressure. Thus, the cuff pressure itself is very important.

A major objective of this invention is to increase the contacting area of the cuff to the finger. Prior art involving the oscillation method was limited to this end by the necessity of having the LED and PTr properly aligned with the blood vessel. No such restrictions apply here. The cuff can fully encompass the bladder and finger, providing a snug fit.

Yet another object of this invention is to incorporate into the cuff a smooth inflatable bladder comprising a single piece of material. This simple design further helps to ensure an adequate fit in which the whole surface area comes in contact with the appendage.

Another object of this invention is to reduce the amount of air that must be pumped into the bladder. The less air needed to secure the finger in the cuff, the more pronounced the changes in the cuff pressure will be during measurement and, thus, the higher the accuracy of the measurement. Therefore, the cuff is initially compressed around the finger manually by pulling the cuff down a slide track. The construction of such a device is in its simplicity which is less expensive than the automated pumping used in the prior art and additionally provides for more accurate results in a cuff oscillation sphygmomanometer.

As, in this embodiment, the left index finger is to be cuffed, it is a further object of the invention to provide a cuff that is adaptable to fit all sizes of fingers. The means for tightening the cuff is provided by a lever attached to the end of the cuff collar. The patient himself can obtain sufficient cuff pressure by inserting his finger into an opening in the cuff and pushing the lever down a guide track. When sufficient force has been applied to the lever in a cuff winding direction, a patient can begin the blood pressure measuring process.

Still another object of this invention is to provide an easily reproducible means of cuff tightening. Since approximately the same amount of force is applied in each simple cuff winding procedure, an operator is practically ensured of properly securing the cuff.

Furthermore, the ease and reproducibility of securing the finger in the cuff, combined with a lack of discomfiture associated with excessive cuff pressure that was too often experienced by the patient in the past, should raise the desirability of blood pressure monitoring.

As demonstrated, a primary object of this invention is to provide a simpler and less expensive cuff. To this end, the cuff oscillation method provides a means for determining blood pressure without employing optical elements such as a light—emitting diode or a phototransistor. The cuff oscillation method, in fact, simply determines arterial volume change by tiny fluctuations in cuff pressure. These fluctuations result from the rise and fall of the blood pressure during the heart cycle. The artery opens when the cuff pressure becomes lower than the blood pressure generated by the beating of the heart. However, the blood pressure, constantly changing between the systolic and diastolic pressures, rises above and falls below the gradually declining cuff pressure until the cuff pressure finally becomes lower than the diastolic blood pressure. The relationship between the opening of the blood vessel and the cuff pressure is called the volumetric change and a volumetric pulse wave can be determined. Further, this pulse wave increases for a period of time, reaches a maximum, and then decreases until the cuff pressure is finally less than the diastolic pressure. When graphed with respect to time and pressure, the amplitudes of the volumetric pulse wave visually represent what is called an envelope of oscillation. Blood pressure is determined by using this envelope curve, which represents tiny fluctuations in the cuff pressure.

Specifically, a cuff for a blood pressure meter has a casing, a cylindrical collar accommodated in the casing, a slide to which one end of the collar is connected, a stopper for the slider, a knob for the slider, a spring for interconnecting the knob and slider, and an indicator for indicating when the deformation of the spring is within a certain amount of displacement.

Other objects and advantages of this invention will become apparent from the following description and accompanying drawings.

BRIEF DESCRIPTION OF THE DRAWINGS

FIG. (1) is a cross-sectional view of the casing, cuff, and sliding mechanism.

FIG. (2A) is a cross-sectional view of a sliding mechanism before cuff pressurization operation.

Figure 1:
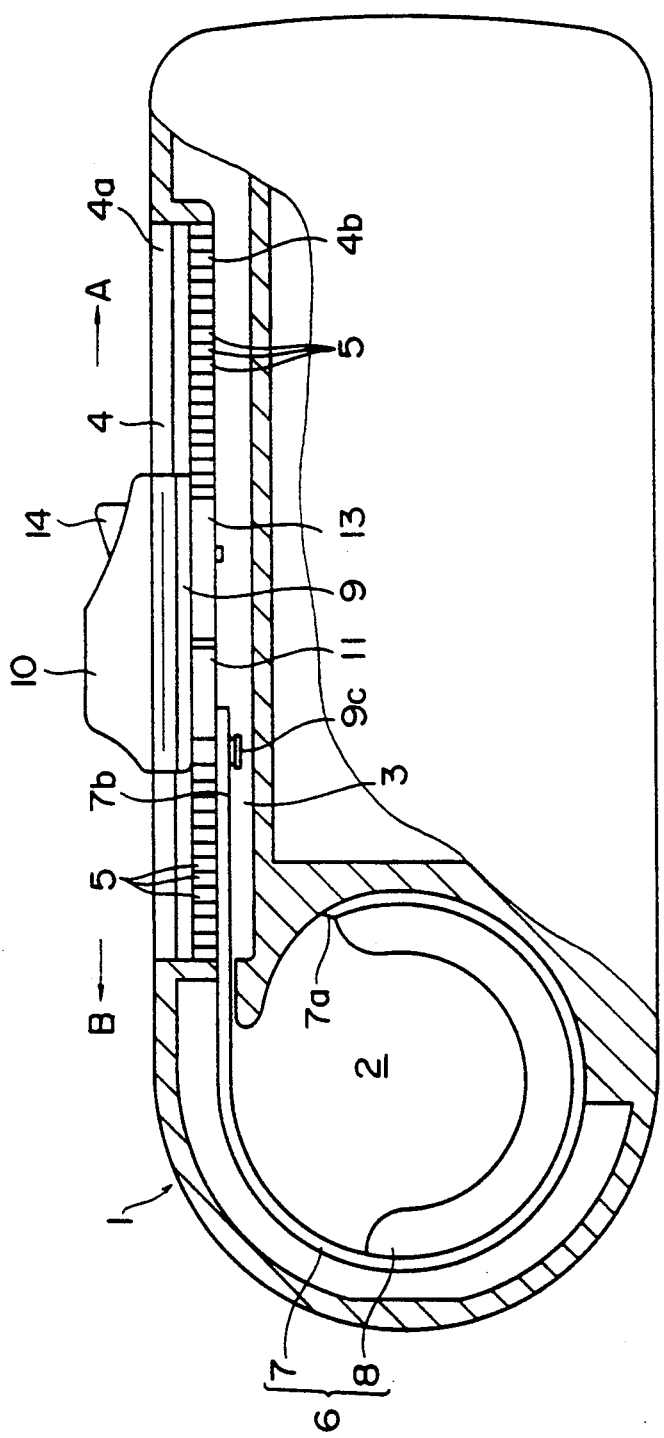

FIG. (2B) is a cross-sectional view of a sliding mechanism after the cuff pressurization operation.

FIG. (3A) is a bottom view of a fixing mechanism for a lever base of the sliding mechanism before cuff pressurization operation.

FIG. (3B) is a bottom view of a fixing mechanism for a lever base of the sliding mechanism after the cuff pressurization operation.

FIG. (4) is a cross-sectional view of the sliding mechanism.

FIG. (5) is a top view of a lever and releasing button of the sliding mechanism.

FIG. (6A) is a bottom view of another embodiment of the fixing mechanism for a lever base of the sliding mechanism before cuff pressurization operation.

FIG. (6B) is a bottom view of another embodiment of the fixing mechanism for a lever base of the sliding mechanism after the cuff pressurization operation.

DETAILED DESCRIPTION OF THE PREFERRED EMBODIMENTS

Referring to FIG. (1), 1 is the casing for the cuff apparatus which, in this embodiment, is made of synthetic resin. An opening 2 in the casing 1 indicates the inside of a cuff 6 and is where a finger should be placed for blood pressure measurement. The cuff 6 consists of two parts, an inflatable bladder 8 and a collar 7. One end of the collar 7a is fixedly attached to the casing 1. The other end 7b extends into a space 3 extending from cuff opening 2 in a cuff winding A direction and is attached to a cuff collar fixing pin 9c, which is part of a lever base 9. The space 3 is capable of receiving circuitry from a blood pressure meter. The bladder 8 is attached to the internal surface of collar 7 and encircles space 2 when the collar 7b is extended in the A direction.

Referring to FIG. (2A) lever base 9, slidable in either the cuff winding A direction or a cuff releasing B direction, is slidably attached to slide a track 4 and placed on top of external step 4a. Another part of the sliding mechanism, movable piece 11, is also slidable in both the cuff winding A or cuff releasing B direction and is mounted to slide track internal step 4b. Additionally provided with slide track 4 are triangular tooth-shaped engagement parts 5 which are used to fix the lever base 9 to the casing 1.

Figure 3A:
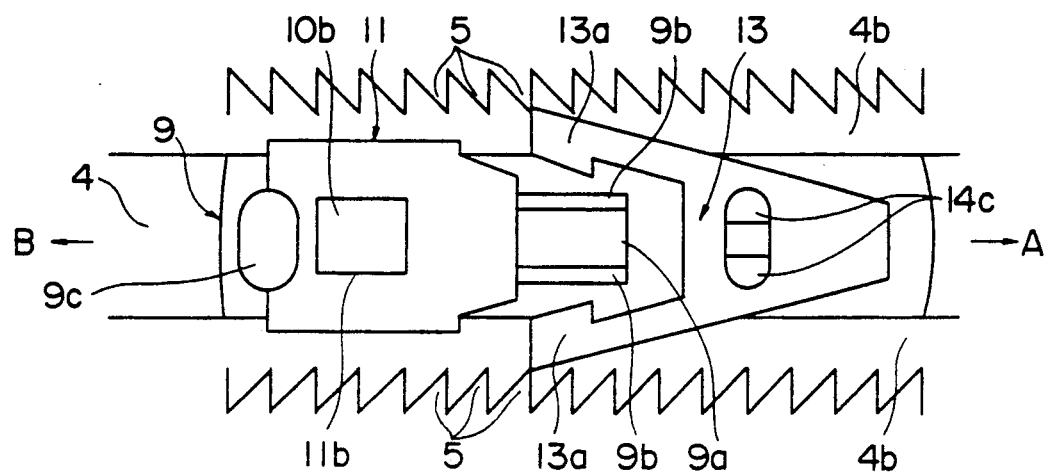
Figure 4:
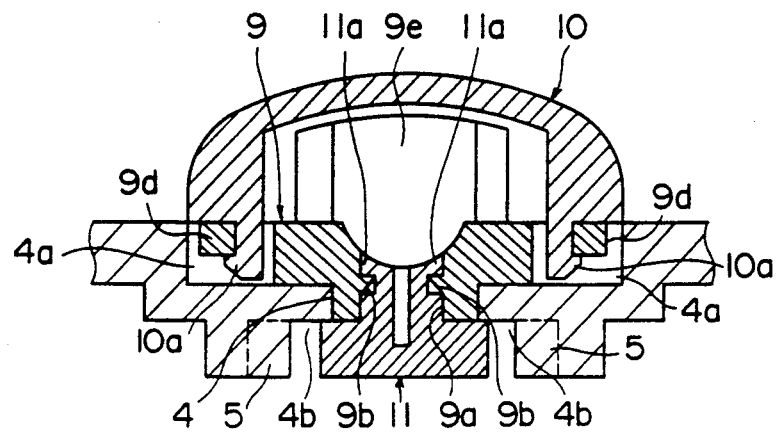
Figure 5:
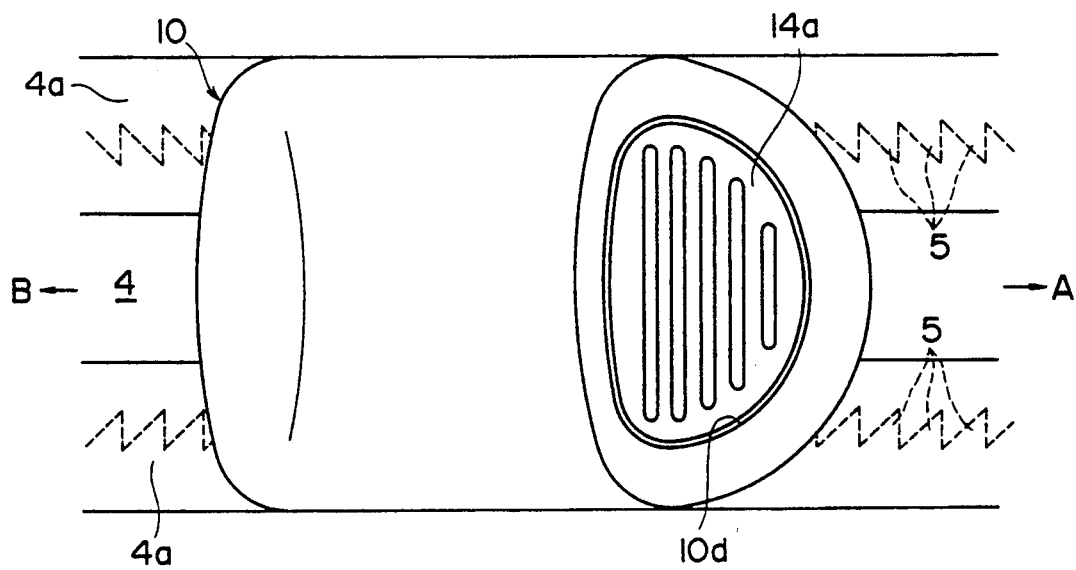

Lever base 9 is connected to a lever 10 by movable piece 11, which is guided in the sliding direction of lever base 9 by guide track 9a. The lever 10 projects outside of the casing 1, enabling the patient to pull the lever base 9 down the slide track 4, and the lever 10 also moves in the cuff winding A and cuff releasing B directions. As depicted in FIG. 3A, the lever 10 and the movable piece are ensured of moving together by a projecting pin 10b projecting through an inserting hole 11b into the slide track 4. Similarly, lever base engaging projection 9b, formed on the inner surface of the guide track 9a, is connected to the movable piece 11 by connecting nails 11a which fit through the guide track 9a and the engaging projections 9b. FIG. 4 illustrates the manner in which lever fixing hook 10a is fixed to the lever base 9 by hooking the fixing part of the lever base 9d.

Figure 2A:
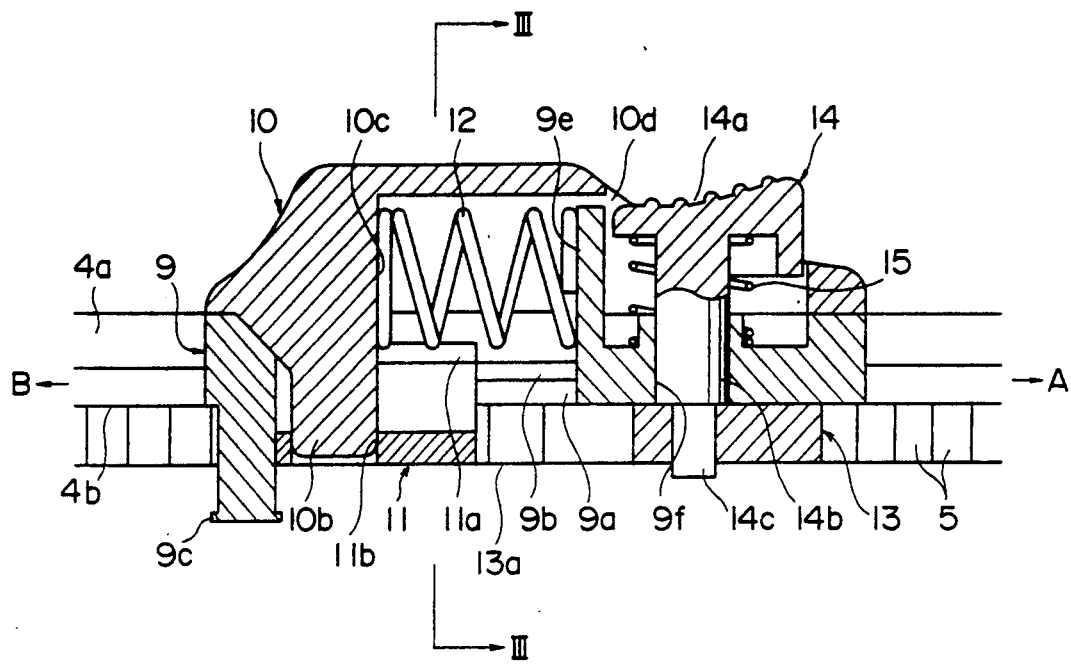

Returning to FIG. 2A, an elastic coilspring 12, biased in the cuff releasing B direction, is placed between lever base internal wall 9e and lever internal wall 10c. However, the embodiment is not limited to a coilspring as any elastic means will suffice. Additionally, lever opening 10d allows head portion 14a of a release button 14 to project above the casing 1. The releasing button 14 is mounted to the lever base 9 by placing the stem portion 14b through insertion hole 9f. The release button end portion 14c has 2 elastic portions which, as is shown in FIG. 3A, are inserted through a bridge shaped engaging hook 13. Once inserted, the elastic button ends 14c expand to effectively fix the engaging hook 13 to the button 14. Furthermore, a coilspring 15 mounted to the release button stem portion 14b outwardly biases the release button so that the hook 13 is normally contacting internal step 4b. Hook tips 13a extend from the hook 13 in order to engage with the engaging portions 5 of the slide track 4, thus preventing the lever base 9 from sliding in the cuff releasing B direction. When the release button 14 is pushed, the hook 13 is downwardly released from the engaging portions 5 and, consequently, lever base 9 becomes slidable in the cuff releasing direction B as well as the cuff winding A direction.

The operation of the cuff wrapping apparatus is as follows. The lever base 9 is initially located near the cuff 6. The diameter of the cuff opening 2 is at this time large so a finger can be easily inserted into the cuff 6. Once the left index finger is inserted, the patient can use his right hand to push the lever 10 in the cuff winding A direction. The force on the lever 10 is then transferred to the lever base 9 through the coilspring 12. Consequently, the lever base 9 also travels in the cuff winding A direction. During this time, the engaging hook tips 13a are deformed in such a manner, i.e. pushed inward, so as to enable movement past the engaging portions 5 and down the slide track 4 in the cuff winding A direction. Thus, the cuff collar 7b is extracted into the cuff extracting space 3 and the cuff 6 is wrapped around the finger.

Figure 2B:
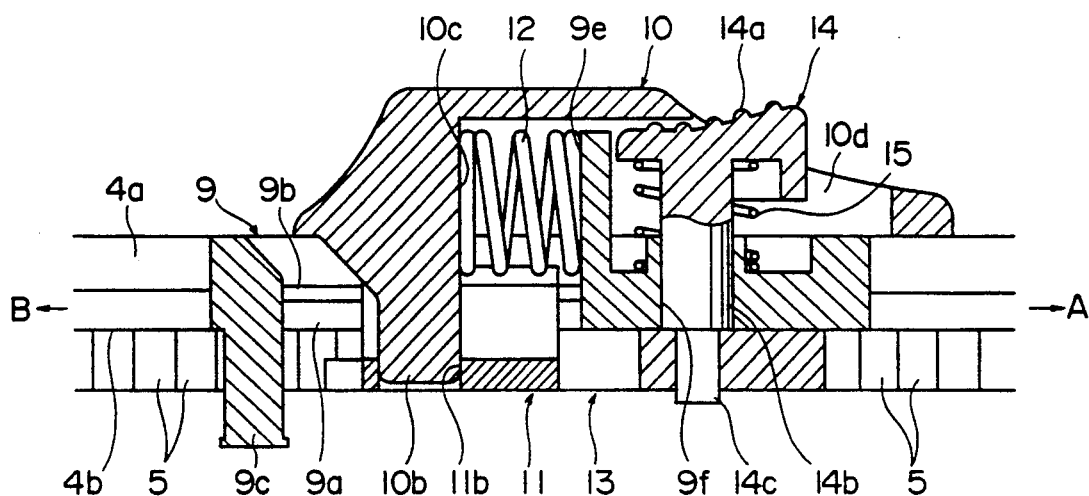
Figure 3B:
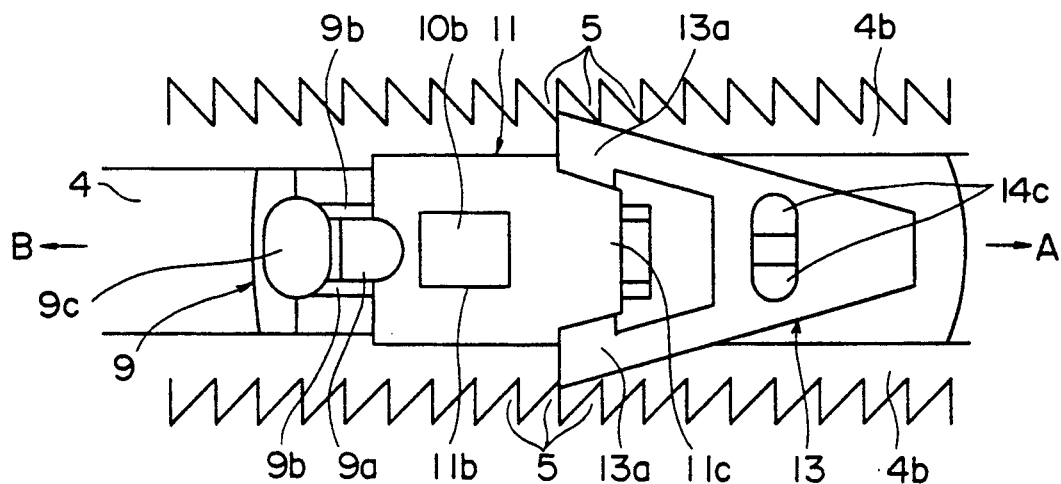

Referring to FIG. 2B, as the cuff 6 is wound and the force applied to the lever 10 gets larger, the coilspring 12 begins to contract. According to the amount of coilspring 12 deformation, the lever 10 is displaced in the cuff winding A direction with respect to the lever base 9. When the lever 10 is displaced, moving piece 11 also begins cuff winding A directional displacement and, as illustrated in FIG. 3B, a moving piece projection 11c goes through the engaging hook tips 13a. At the time when the most suitable winding force is applied, the projection 11c is engaged with the engaging hook tips 13a, consequently preventing further deformation of the tips 13a. Thus, even if more force is exerted on the lever 10, the hook tips 13a can not even surpass the next engaging portion 5. Accordingly, the lever base 9 is fixed.

Once the lever base 9 is fixed, the patient takes his hand off the lever 10, which returns to its original position with respect to the lever base 9 due to the force from the coilspring 12. At this time, the moving piece projection 11c disengages from the hook tips 13a, but the lever base 9 is still secured because the hook tips 13a cannot move down the slide track 4 in the cuff releasing B direction. Finally, the inflatable bladder 8 is filled with air to compress the finger and the process of blood pressure measurement begins.

After the completion of the blood pressure measurement, the release button 14 is pushed. In turn, the engaging hook 13 drops below internal step 4b into a hollow part of the casing 1. Thus, the hook tips 13a are no longer engaged with the engaging portions 5 and the lever base 9 is now freed to move in the cuff releasing B direction to loosen the cuff 6. When the release button 14 is no longer pushed, coilspring 15 will return the release button to its original position. Consequently, the hook 13 will return to the internal step 4b and the hook tips will reengage with the engaging projections 5.

Figure 6A:
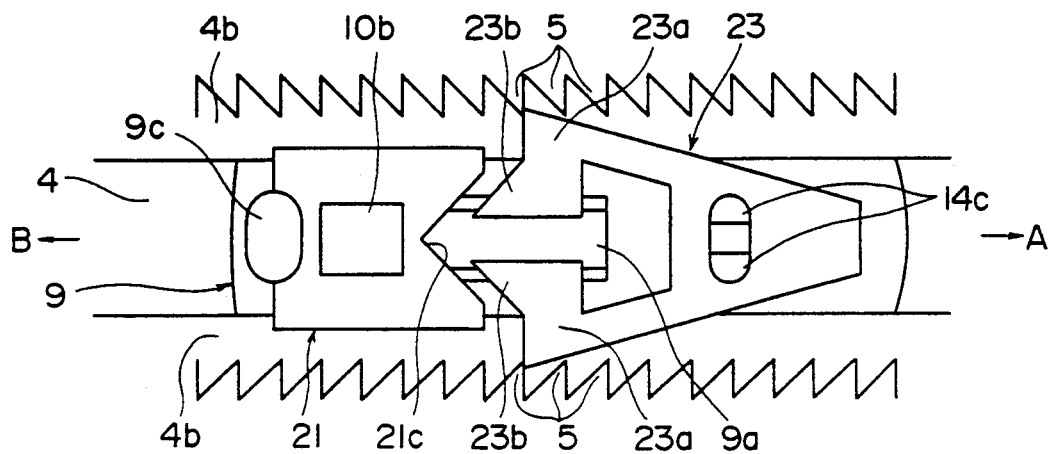
Figure 6B:
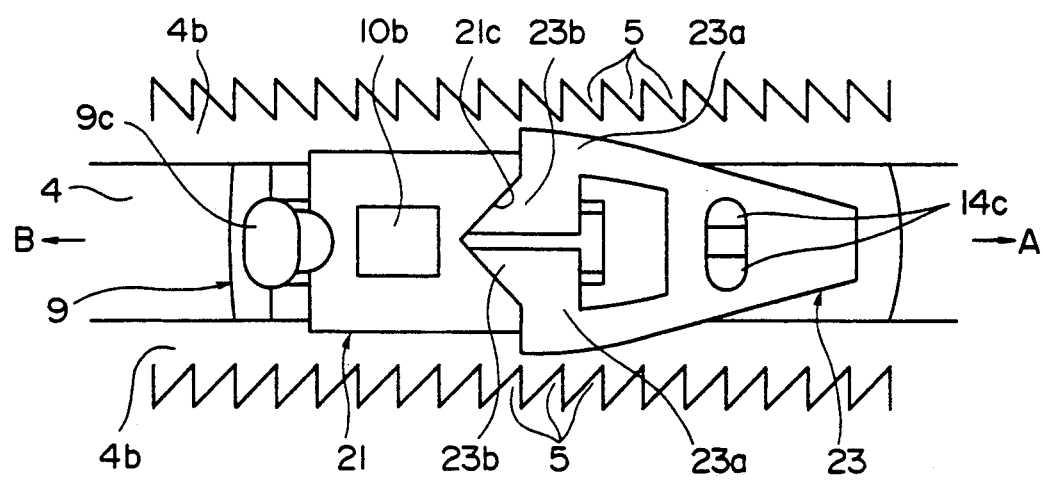

FIGS. 6A and 6B illustrate another embodiment of this invention. The only difference is the shape of movable piece 21 and engaging hook 23. Recess 21c is formed in the movable piece 21 while engaging tips 23a have projections 23b formed thereon. During the cuff winding process, the recess 21c and the tip projections 23b are apart from each other when the force applied to the lever 10 is small. Therefore, the unrestricted hook tips 23a are able to be deformed in such a manner as to allow them to pass the engaging projections 5 in the cuff winding A direction. Consequently, the lever base 9 moves in the A direction and the cuff 6 is wound. As the force applied to the lever 10 gets larger, the movable piece recess 21c gets closer to the tip projections 23b. When the winding force of the cuff surpasses an appropriate value, the tip projections 23b fit into the recess 21c as shown in FIG. 6b. However, since the hook tips 23a are no longer in contact with the engaging portions 5, the lever base 9 will recede a little bit in the cuff releasing B direction. Subsequently, the hook projections 23b will begin to slide out of the recess 21c until the hook tips again engage with the engaging projections 5. At this time the lever base is fixed and blood pressure can be measured.

The above description and accompanying drawings are merely illustrative of the applications of the principles of the present invention and are not limiting. Many other embodiments falling under the spirit and scope of this invention may be devised by those skilled in the art. Accordingly, this invention is only limited by the scope of the appended claims.

What is claimed is:

1. A cuff mechanism for a blood pressure meter, comprising:
   a) a casing;
   b) a cuff having first and second ends, the first end of the cuff being connected to the casing;
   c) a lever base movable in cuff winding and cuff releasing directions in the casing, the second end of the cuff being connected to the lever base;
   d) a lever positioned on the lever base and movable therewith;
   e) an elastic body positioned between the lever base and the lever for transferring force applied to the lever;
   f) a slide track located in the casing;
   g) a lever base fixing mechanism for fixing the lever base to the casing including a release button, a hook with hook tips thereon, a plurality of engaging projections connected to the slide track and engagable with the hook tips, and a moving piece projection for selectively securing and releasing the hook tips to the engaging projections, in accordance with the release button;
   h) a movable piece movable with the lever enabling the lever base fixing mechanism to selectively enter a fixing state and a releasing state in response to a degree of deformation of the elastic body.

2. The cuff mechanism according to claim 1, further comprising a collar having one end affixed to the casing, and an inflatable bladder positioned in the collar.

3. The cuff mechanism according to claim 1, including a hollow space for receiving circuitry from a blood pressure meter.

4. The cuff mechanism according to claim 1, further comprising a projecting pin for connecting the lever to the movable piece.

5. The cuff mechanism according to claim 1, wherein the lever further comprises a lever fixing hook for hooking the lever to the lever base.

6. The cuff mechanism according to claim 5, wherein the lever base further comprises a fixing part for hooking the lever fixing hook to the lever base.

7. The cuff mechanism according to claim 1, wherein the lever base further comprises a fixing part for hooking the lever to the lever base.

8. The cuff mechanism according to claim 1, wherein the elastic body comprises a coilspring.

9. The cuff mechanism according to claim 1, wherein the release button comprises a head portion projected above the casing.

10. The cuff mechanism according to claim 1, further comprising a coilspring for returning the release button to an original position whenever the release button is not under pressure.

11. The cuff mechanism according to claim 1, further comprising a guide track for guiding the movable piece.

12. The cuff mechanism according to claim 11, further comprising a lever base engaging projection on an inner surface of the guide track.

13. The cuff mechanism according to claim 12, further comprising connecting nails for connecting the lever base engaging projection to the movable piece.

14. A method of measuring blood pressure comprising:
   a) placing a casing on a user's finger;
   b) surrounding the finger at least partially with a cuff including a collar and a bladder;
   c) moving a lever in a cuff winding direction to secure the cuff on the finger.
   d) transferring a force resulting from the moving step to a lever base using an elastic body connected to the lever;
   e) fixing the collar in a fixed state by moving a moving piece projection against hook tips of a hook which is connected to the lever base, thereby engaging the back tips with engaging projections connected to the casing; and
   f) placing the collar in a releasable state by pushing a release button to disengage the hook tips from the engaging projections.

15. A method of measuring blood pressure according to claim 14 further comprising the step of switching from the release state to the fixed state in response to a degree of deformation of the elastic body.

16. A cuff mechanism for a blood pressure meter, comprising:
   a) a casing;
   b) a cuff having first and second ends, the first end of the cuff being connected to the casing;
   c) a lever base movable in cuff winding and cuff releasing directions in the casing, the second end of the cuff being connected to the lever base;
   d) a lever positioned on the lever base and movable therewith;
   e) an elastic body positioned between the lever base and the lever for transferring force applied to the lever;
   f) a slide track located in the casing;
   g) a lever base fixing mechanism for fixing the lever base to the casing including a release button, a hook having hook tips thereon and a plurality of hook tip projections, a plurality of engaging projections connected to the slide track for engaging the hook tips, and a recess for receiving the hook tip projections permitting release of the hook tips from the track projections;
   h) a movable piece movable with the lever enabling the lever base fixing mechanism to selectively enter a fixing state and a releasing state in response to a degree of deformation of the elastic body.

17. The cuff mechanism according to claim 16, wherein the release button comprises a head portion projected above the casing.

18. The cuff mechanism according to claim 16, further comprising a coilspring for returning the release button to an original position whenever the release button is not under pressure.

* * * * *